(12) United States Patent
Akura

(10) Patent No.: US 9,968,442 B2
(45) Date of Patent: May 15, 2018

(54) ACCOMMODATING INTRAOCULAR LENS

(71) Applicants: Frontier Vision Co., Ltd., Hyogo (JP); Junsuke Akura, Wakayama (JP)

(72) Inventor: Junsuke Akura, Wakayama (JP)

(73) Assignee: MIRAI EYE INC., Hyogo (JP)

( * ) Notice: Subject to any disclaimer, the term of this patent is extended or adjusted under 35 U.S.C. 154(b) by 101 days.

(21) Appl. No.: 15/103,540

(22) PCT Filed: Dec. 10, 2014

(86) PCT No.: PCT/JP2014/082738
§ 371 (c)(1),
(2) Date: Jun. 10, 2016

(87) PCT Pub. No.: WO2015/087931
PCT Pub. Date: Jun. 18, 2015

(65) Prior Publication Data
US 2016/0310263 A1    Oct. 27, 2016

(30) Foreign Application Priority Data

Dec. 13, 2013    (JP) ................................. 2013-257870

(51) Int. Cl.
*A61F 2/16*    (2006.01)
(52) U.S. Cl.
CPC ........ *A61F 2/1635* (2013.01); *A61F 2/16015* (2015.04); *A61F 2/1648* (2013.01);
(Continued)
(58) Field of Classification Search
CPC ............ A61F 2/1635; A61F 2002/1682; A61F 2/1648; A61F 2/1694; A61F 2/1627; A61F 2250/0003
See application file for complete search history.

(56) References Cited

U.S. PATENT DOCUMENTS 7,462,193 B2 * 12/2008 Nagamoto ............ A61F 2/1613
    623/4.1
7,883,540 B2    2/2011 Niwa et al.
(Continued)

FOREIGN PATENT DOCUMENTS

JP    2006-516002 A    6/2006
JP    2007-89810 A    4/2007
(Continued)

OTHER PUBLICATIONS

International Search Report dated Mar. 10, 2015 issued in corresponding PCT/JP2014/082738 application (2 pages).
(Continued)

*Primary Examiner* — David H Willse
*Assistant Examiner* — Javier Blanco
(74) *Attorney, Agent, or Firm* — Millen, White, Zelano & Branigan, P.C.; William Nixon

(57) ABSTRACT

An intraocular lens includes a lens capsule expanding device and an optical portion. A front supporting portion makes contact with an inner surface of an anterior capsule. A rear supporting portion makes contact with an inner surface of a posterior capsule while facing the front supporting portion. A connecting portion connects the front supporting portion and the rear supporting portion so as to have a biasing force to separate the front supporting portion and the rear supporting portion. Due to the biasing force, the front supporting portion presses the inner surface of the anterior capsule and the rear supporting portion presses the inner surface of the posterior capsule. The optical portion changes the curvature of a central portion according to movement of the connecting portion that moves the front supporting portion and the rear supporting portion closer to or away from each other with movement of the lens capsule.

3 Claims, 5 Drawing Sheets

(52) U.S. Cl.
CPC .......... *A61F 2/1694* (2013.01); *A61F 2/1627* (2013.01); *A61F 2002/1682* (2015.04); *A61F 2250/0003* (2013.01)

(56) References Cited

U.S. PATENT DOCUMENTS

| | | | |
|---|---|---|---|
| 8,048,155 B2* | 11/2011 | Shadduck | A61F 2/1648 623/6.13 |
| 8,603,166 B2 | 12/2013 | Park | |
| 8,834,566 B1 † | 9/2014 | Jones | |
| 8,852,275 B2 | 10/2014 | Park | |
| 9,220,591 B2* | 12/2015 | Zhao | A61F 2/1635 |
| 2002/0002404 A1* | 1/2002 | Sarfarazi | A61F 2/1613 623/6.34 |
| 2004/0082993 A1 | 4/2004 | Woods | |
| 2009/0012609 A1 | 1/2009 | Geraghty et al. | |
| 2009/0018652 A1* | 1/2009 | Hermans | A61F 2/1613 623/6.38 |
| 2009/0043384 A1 | 2/2009 | Niwa et al. | |
| 2009/0306774 A1 | 12/2009 | Park | |
| 2010/0016963 A1 | 1/2010 | Park | |
| 2010/0179653 A1* | 7/2010 | Argento | A61F 2/1635 623/6.13 |
| 2011/0071628 A1* | 3/2011 | Gross | A61F 2/1629 623/6.51 |
| 2011/0295368 A1* | 12/2011 | Betser | A61F 2/1629 623/6.43 |
| 2012/0310345 A1 | 12/2012 | Olcina Portilla | |
| 2012/0330415 A1* | 12/2012 | Callahan | A61F 2/1694 623/6.43 |
| 2013/0317607 A1 | 11/2013 | Deboer et al. | |
| 2014/0180410 A1* | 6/2014 | DeVita Gerardi | A61F 2/1635 623/6.37 |
| 2016/0361157 A1* | 12/2016 | Honigsbaum | A61F 2/1629 |

FOREIGN PATENT DOCUMENTS

| | | |
|---|---|---|
| JP | 2010-502358 A | 1/2010 |
| JP | 2010-520011 A | 6/2010 |

OTHER PUBLICATIONS

English Abstract of JP 2007-089810 A published Apr. 12, 2007 (2 pages).
English Abstract of JP 2010-502358 A published Jan. 28, 2010 (2 pages).
English Abstract of JP 2010-520011 A published Jun. 10, 2010 (1 page).

* cited by examiner
† cited by third party

ACCOMMODATING INTRAOCULAR LENS

TECHNICAL FIELD

The present invention relates to an accommodating intraocular lens which is inserted into a lens capsule of which the anterior capsule is incised during ophthalmic surgeries such as an extracapsular extraction surgery performed as a part of a cataract surgery, a refractive correction surgery, or a presbyopia correction surgery.

BACKGROUND ART

Generally, the focus accommodation of the human eyes (hereinafter simply referred to as "accommodation") is realized by changing the thickness of the lens. As illustrated in FIG. 5, a lens L is a convex transparent member having a diameter of approximately 9 to 10 mm and a thickness of approximately 4 to 5 mm and exerting a lens function, and is fixed to a ciliary body C by Zinn's zonules Z in such a manner as to be arranged on the rear side of the iris I in a state of being encapsulated by a lens capsule S.

A detailed accommodation mechanism will be described. For example, when a person looks at a distant object, as illustrated in FIG. 5(a), the ciliary muscles Cm of the ciliary bodies C are relaxed and the ciliary bodies C are at positions retracted in a direction away from the lens capsule S. In this state, relatively strong tension is generated in the Zinn's zonules Z positioned between the ciliary bodies C and the lens equators Se. As a result, the lens equators Se are pulled in a radially outward direction to deform the lens L in such a way as to decrease the thickness thereof. Accordingly, the thickness of the lens L in the lens capsule S decreases, whereby the focus accommodation during distance vision is realized.

On the other hand, when accommodation is realized to view a near object, as illustrated in FIG. 5(b), the ciliary muscles Cm of the ciliary bodies C are contracted so that the ciliary bodies C protrude centripetally (toward the lens equators Se) and the ciliary bodies C are positioned in a direction closer to the lens capsule S. As a result, since the tension of the Zinn's zonules Z decreases, the thickness of the lens L increases due to the elasticity inherent to the lens, whereby the focus accommodation during near vision is realized. During this focus accommodation, it is known that the closer a portion is located in relation to the center of the anterior capsule Sf, the more the portion is likely to be movable, whereas the posterior capsule Sb is rarely movable.

As described above, the thickness of the lens is changed according to contraction and relaxation of the ciliary muscles of the ciliary bodies to refract light entering the eyes, whereby the focus accommodation is realized. In this accommodation mechanism, it is known that the contraction and relaxation functions of the ciliary muscles of the ciliary bodies are maintained satisfactorily in old ages in the same manner as in young ages. On the other hand, it is also known that, since the contents of the lens and the lens capsule become hardened in old ages and lose flexibility, thus making the thickness of the lens rarely change, the ability (hereinafter referred to as accommodation power) to accommodate the focus range freely from distance vision to near vision is lost (this is referred to as presbyopia).

By the way, a disease called a cataract which is a clouding of the lens mainly resulting from aging is one of the diseases occurring in the lens, and many patients have cataract surgery to treat their cataracts. This surgery generally uses a method in which the anterior capsule is incised in a circular form to create a circular hole, the contents of the cloudy lens are extracted from the hole according to phacoemulsification, and an intraocular lens is inserted into a transparent lens capsule while leaving only the lens capsule with the circular hole formed therein. The cataract surgery based on this method has been currently applied to more than one million patients in Japan every year and more than 3 million patients in the United States of America every year, and the intraocular lenses used for this surgery are generally monofocal lenses.

However, since the monofocal lenses are generally formed of a material such as polymethylmethacrylate (PMMA), silicon, or acryl, and it is not possible to change the thickness of the monofocal lens itself, the loss of the accommodation power after the surgery is unavoidable. In contrast, multifocal lenses which are arranged in a refractive multifocal lens having portions having different refractive powers formed concentrically in an optical portion and a diffractive multifocal lens having a structure causing an optical diffraction phenomenon formed in an optical portion so as to disperse and capture light entering into the eyes are arranged as multifocal lenses for distance vision and near vision (in some cases, for intermediate vision). However, these multifocal intraocular lenses have not reached a sufficient point of satisfaction to meet the demands of patients because there are reports that some patients experience halos where a ring of light appears around an object, trouble such as glare with bright light, a decrease in vision, and insufficient contrast sensitivity.

Moreover, in recent years, as an intraocular lens capable of exerting an accommodation function by a method different from the above-mentioned method, an accommodating intraocular lens including an optical portion formed of a convex lens and two joint-type connection arms arranged in such a manner as to come into contact with the inner side of a lens equator so that accommodation is realized by the optical portion moving back and forth is known (see Patent Document 1 below). In this accommodating intraocular lens, the connection arm is attached to the optical portion at a first position on the connection arm and works harmoniously with the movement of the equator of the lens capsule to which the contraction and relaxation of the ciliary muscles of the ciliary bodies are transmitted via the Zinn's zonules at a second position on the connection arm.

On the other hand, a number of ring-shaped lens capsule expanding devices which are used for expanding the lens capsule before inserting an intraocular lens during cataract surgery have been proposed. These ring-shaped lens capsule expanding devices come in two types depending on the purpose.

One example is called a capsular tension ring (a lens capsule expansion ring) which is an open ring formed in a C-shape. This ring is inserted from the inner side into the lens equators in which the Zinn's zonules are weak and ruptured to expand the lens equators outward to create a round shape.

The other example is called an equator ring which is formed in an O-shape. This ring is a relatively thick closed ring (continuous ring) of which the cross-section has sharp edges such as a square. This ring is arranged on an inner side of the lens equators to form a strong bent portion in the lens capsule to prevent the growth and entrance of lens epithelial cells.

CITATION LIST

Patent Document

Patent Document 1: Japanese Unexamined Patent Application Publication No. 11-47168

SUMMARY OF THE INVENTION

Problem to be Solved by the Invention

However, the focus accommodation function of the human eyes is exerted based on the contraction and relaxation of the ciliary muscles of the ciliary bodies. Therefore, in order to move the optical portion of an intraocular lens in a front-back direction, it is necessary to deform the lens capsule by accurately transmitting slight contraction and relaxation of the ciliary muscles of the ciliary bodies. To realize this, it is important that the Zinn's zonules that transmit the contraction and relaxation of the ciliary muscles of the ciliary bodies to the lens capsule continuously have tension of moderate strength, and as a result, the lens capsule has moderate strength.

In this regard, a conventional accommodating intraocular lens does not act such that the Zinn's zonules continuously have tension of moderate strength. Therefore, the slight contraction and relaxation of the ciliary muscles of the ciliary bodies are not accurately transmitted to the lens capsule and are not accurately converted to the movement of the optical portion in the front-back direction. Moreover, it is difficult to accurately exert the accommodation function of the intraocular lens arranged therein.

Similarly, the ring-shaped lens capsule expanding device can adjust the position of the lens equator and create a strong bent portion in the lens capsule. However, it is difficult to continuously maintain tension of moderate strength in the Zinn's zonules. Moreover, the ring-shaped lens capsule expanding device expands the lens equator outward to weaken the tension of the Zinn's zonules. For this reason, the slight contraction and relaxation of the ciliary muscles of the ciliary bodies are not accurately transmitted to the lens capsule, and it is difficult to exert the accommodation function of the accommodating intraocular lens.

Further, in a large number of conventional ring-shaped lens capsule expanding devices, the connection arm and the ring-shaped lens capsule expanding device itself are fixed in such a manner to be in contact with the inner side of the lens equator. Thus, the anterior capsule and the posterior capsule adhere to each other to block the lens equator with time. In recent years, it has been found that, since a secondary cataract rarely occurs when hydatoid always flows into the lens equator, the hydatoid has an effect of suppressing the growth of lens epidermal cells. However, in these conventional intraocular lenses, since the lens equator is not exposed to hydatoid, lens epidermal cells grow in the lens equator to cause fibroplasia, thus creating a state in which a secondary cataract occurs easily.

When a secondary cataract occurs, since the central portion of the lens capsule becomes cloudy and light can rarely pass through the lens capsule, the visual power decreases and the lens equator adheres in the front-back direction to cause fibroplasia, which results in hardening of the equator. Moreover, the joint-type connection arm of the accommodating intraocular lens is fixed by fibers and becomes immovable, which prevents exertion of the accommodation function of the accommodating intraocular lens.

The present invention was made in view of the aforementioned problems and aims to provide an accommodating intraocular lens capable of exerting the focus accommodation power accurately and sufficiently and preventing the occurrence of a secondary cataract.

Solution to Problems

In order to attain the object, an accommodating intraocular lens according to the present invention is an accommodating intraocular lens inserted into a lens capsule from which contents are removed during an ophthalmic surgery, including: a lens capsule expanding device; and an optical portion which is elastically deformable. The lens capsule expanding device including: a front supporting portion provided in such a manner as to make contact with an inner surface of an anterior capsule so as to pass light toward a rear side; a rear supporting portion provided on a rear side of the front supporting portion in such a manner as to make contact with an inner surface of a posterior capsule while facing the front supporting portion so as to pass light from the front side toward a rear side; and a connecting portion connecting the front supporting portion and the rear supporting portion in such a manner as to have biasing force in a direction of separating the front supporting portion and the rear supporting portion from each other, wherein due to the biasing force of the connecting portion, the front supporting portion presses the inner surface of the anterior capsule and the rear supporting portion presses the inner surface of the posterior capsule. The optical portion has a front ring member and a rear ring member provided on a front surface and a rear surface in such a manner of being parallel to a circumferential portion of the optical portion, and the front ring member is connected to an upper portion of the connecting portion of the lens capsule via a lateral branch and the rear ring member is connected to a lower portion of the connecting portion of the lens capsule expanding device via a lateral branch. Force is applied to the optical portion in a backward direction from the connecting portion via the front ring member and force is applied to the optical portion in a forward direction from the connecting portion via the rear ring member according to movement of the connecting portion when the front supporting portion and the rear supporting portion move in a direction away from each other with movement of the lens capsule whereby the optical portion is compressed between the front ring member and the rear ring member and the curvature of the optical portion is changed. According to this configuration, since force is applied from the connecting portion to the optical portion via the front ring member and the rear ring member in a direction of compressing the optical portion to change the curvature of the optical portion, the focus accommodation power can be exerted with higher accuracy and sufficiently.

Moreover, the connecting portion may include a front ring connecting portion and a rear ring connecting portion, and the front ring member may be connected to the upper portion of the front ring connecting portion via the lateral branch and the rear ring member may be connected to the lower portion of the rear ring connecting portion via the lateral branch. According to this configuration, since force is applied from the front ring connecting portion and the rear ring connecting portion of the connecting portion to the optical portion via the front ring member and the rear ring member in a direction of compressing the optical portion to change the curvature of the optical portion, the focus accommodation power can be exerted with higher accuracy and sufficiently.

In order to attain the object, another accommodating intraocular lens according to the present invention is an accommodating intraocular lens inserted into a lens capsule from which contents are removed during an ophthalmic surgery, including: a lens capsule expanding device; and an optical portion which is elastically deformable. The lens capsule expanding device including: a front supporting portion provided in such a manner as to make contact with an inner surface of an anterior capsule so as to pass light toward a rear side; a rear supporting portion provided on a rear side of the front supporting portion in such a manner as to make contact with an inner surface of a posterior capsule while facing the front supporting portion so as to pass light from the front side toward a rear side; and a connecting portion connecting the front supporting portion and the rear supporting portion in such a manner as to have biasing force in a direction of separating the front supporting portion and the rear supporting portion from each other, wherein due to the biasing force of the connecting portion, the front supporting portion presses the inner surface of the anterior capsule and the rear supporting portion presses the inner surface of the posterior capsule. The optical portion has a rear ring member provided on a rear surface in such a manner of being parallel to a circumferential portion of the optical portion, and the rear ring member is connected to a lower portion of the connecting portion of the lens capsule expanding device via a lateral branch. Force is applied to the optical portion in a forward direction from the connecting portion via the rear ring member according to movement of the connecting portion when the front supporting portion and the rear supporting portion move in a direction away from each other with movement of the lens capsule whereby the optical portion is compressed between the rear ring member and the front supporting portion of the lens capsule expanding device and the curvature of the optical portion is changed. According to this configuration, since force is applied from the connecting portion to the optical portion in the forward direction via the rear ring member to compress the optical portion between the rear ring member and the front supporting portion of the lens capsule expanding device to change the curvature of the optical portion, the focus accommodation power can be exerted with higher accuracy and sufficiently.

Moreover, the lens capsule expanding device may have a convex lens or a concave lens provided in the rear ring member or the front ring member and having a refractive power corresponding to a symptom of a patient.

Moreover, the optical portion may be formed of an elastic film which can be expanded and contracted and has a predetermined thickness, and a flowable substance may be filled in the elastic film. According to this configuration, since the optical portion can be easily deformed when force is applied directly or indirectly from the connecting portion to the optical portion, it is possible to effectively change the curvature of the optical portion.

Moreover, the circumferential portion of the optical portion may have a thickness of 20 to 100 μm, a central portion of the optical portion may have a thickness of 5 to 20 μm, and the circumferential portion may be thicker than the central portion. Particularly, it is preferable that the optical portion is formed so that the thickness of the elastic film gradually increases as it advances from the circumferential portion toward the central portion. According to this configuration, a local deformation of the circumferential portion of the optical portion decreases, and the circumferential portion is likely to be deformed generally uniformly. As a result, the central portion of the optical portion is also likely to be deformed uniformly. Moreover, since the central portion of the optical portion is likely to be deformed due to a small thickness, the curvature of the optical portion can be changed effectively.

Moreover, the optical portion may have a bulging portion formed at a front end and/or a rear end of the thick portion of the elastic film so as to swell toward an inner side. According to this configuration, when the optical portion is deformed, the circumferential portion of the optical portion is easily constricted near the bulging portion. As a result, since the central portion of the optical portion is likely to swell, the curvature of the optical portion can be changed effectively.

Moreover, the optical portion may be formed so that a refractive index of the flowable substance gradually increases toward the center of the optical portion. For example, the optical portion may be partitioned in the front-back direction and a segment including the center of the optical portion may have a larger refractive index than the refractive indices of the other segments. According to this configuration, since the closer to the center, the larger the refractive index like a human lens, it is possible to create a large change in the refractive index by a small deformation of the optical portion.

Moreover, the optical portion may have a core member formed at the center and having a larger rigidity than the flowable substance. According to this configuration, when the optical portion applies force directly or indirectly from the connecting portion, since the flowable substance present around the core substance applies force to the elastic film efficiently, the curvature of the optical portion can be changed efficiently.

Moreover, the core member may be a convex lens having a refractive power corresponding to a symptom of a patient. According to this configuration, the optical portion can be used for the purpose of obtaining the accommodation power mainly, and the convex lens provided in the optical portion can be used for the purpose of obtaining a refractive power corresponding to the symptom of a patient. Moreover, it is possible to reduce a refraction error (a difference between a target refractive value before surgery and an actual refractive value after surgery) of the refractive power after surgery.

Moreover, the optical portion may have an injector for injecting the flowable substance into the optical portion. According to this configuration, after the optical portion is folded and inserted into the lens capsule expanding device in a state in which no or a small amount of the flowable substance is present in the optical portion, since the flowable substance can be injected into the optical portion through the injector, it is possible to reduce the size of an incised wound for inserting the accommodating intraocular lens into the lens capsule. Moreover, the refractive power after surgery can be easily adjusted to a target refractive power by injecting or sucking the flowable substance from the injector when a refraction error occurs after surgery.

Moreover, the lens capsule expanding device may have a convex lens or a concave lens provided in the rear supporting portion and having a refractive power corresponding to a symptom of a patient. According to this configuration, the optical portion which is elastically deformable can be used for the purpose of obtaining the accommodation power mainly, and the convex lens or the concave lens provided in the rear supporting portion can be used for the purpose of obtaining a refractive power corresponding to the symptom of a patient. Due to this, the optical portion which is elastically deformable is easily folded when it is formed in a flat shape and can be inserted into the eye from a small incised wound of the lens capsule. Moreover, since the convex lens or the concave lens provided in the rear supporting portion supplements the refractive power after surgery mainly, it is possible to reduce a refraction error (a difference between a target refractive value before surgery and an actual refractive value after surgery) of the refractive power after surgery.

Effects of the Invention

According to the present invention, due to the biasing force of the connecting portion, the front supporting portion presses the inner surface of the anterior capsule and the rear supporting portion presses the inner surface of the posterior capsule. As a result, the peripheral portion of the lens equator tries to extend and expand in the front-back direction and the lens equator expands. At the same time, the lens equator moves centripetally and the diameter of the lens equator decreases. Due to this, the Zinn's zonules are pulled in both directions toward the lens capsule and the ciliary bodies and tension of moderate strength is continuously applied to the Zinn's zonules. As a result, moderate tension is applied to the lens capsule. Thus, the Zinn's zonules can transmit the slight contraction and relaxation of the ciliary muscles of the ciliary bodies to the lens capsule with high accuracy, and accordingly, the accommodation function of the optical portion disposed therein can be exerted with high accuracy.

Moreover, when the front supporting portion is formed in an open state like a ring form, hydatoid flows from an anterior capsule incision portion to the space between the front supporting portion and the connecting portion and flows into the lens capsule, and the lens equator is exposed to the hydatoid. Thus, the growth or fibroplasia of the lens epithelial cells in the lens equator is suppressed and the occurrence of the secondary cataract can be prevented.

Further, when the front supporting portion and the rear supporting portion move in the direction closer to or away from each other according to the movement of the lens capsule, since force is applied from the connecting portion to the optical portion via the front ring member and the rear ring member in a direction of compressing the optical portion to change the curvature of the optical portion, the focus accommodation power can be exerted with higher accuracy and sufficiently.

MODE FOR CARRYING OUT THE INVENTION

<First Embodiment>

Figure 1A:
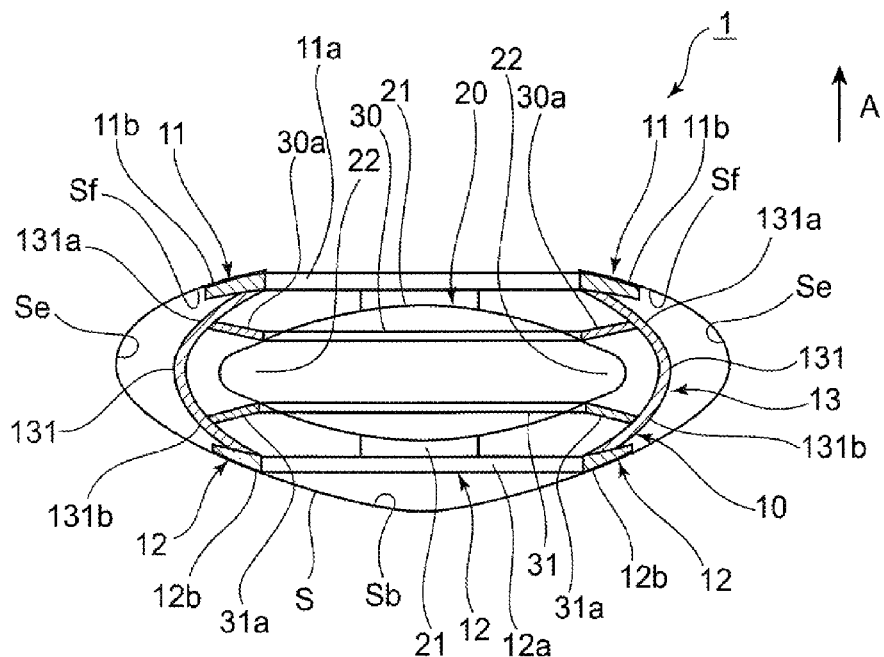
FIG. 1(a) is a longitudinal cross-sectional view illustrating an accommodating intraocular lens according to a first embodiment of the present invention.

Next, a first embodiment of an accommodating intraocular lens according to the present invention will be described with reference to FIG. 1.

An accommodating intraocular lens 1 includes a lens capsule expanding device (hereinafter referred to as a device 10) and an optical portion 20 disposed inside the device 10. In the following description, the direction indicated by arrow A illustrated in the drawings is defined as a front side and the opposite direction is defined as a rear side.

[Device Configuration]

As illustrated in FIG. 1, the device 10 is arranged in the lens capsule S of which the anterior capsule Sf is incised during ophthalmic surgeries such as an extracapsular extraction surgery performed as a part of a cataract surgery, a refractive correction surgery, or a presbyopia correction surgery. As illustrated in FIG. 1, the device 10 includes a front supporting portion 11 positioned on the front side in the lens capsule S, a rear supporting portion 12 positioned on the rear side in the lens capsule S, and a connecting portion 13 that connects the front supporting portion 11 and the rear supporting portion 12.

As illustrated in FIG. 1, the front supporting portion 11 is a ring-shaped elastic member having an opening 11a at the center. The front supporting portion 11 has an inclined surface 11b disposed on the front surface side so as to be gradually inclined toward the rear side as it advances from an inner circumferential portion toward an outer circumferential portion. Due to this, since the front supporting portion 11 is provided in such a manner as to make contact with the inner surface of the anterior capsule Sf of the lens capsule S during a cataract surgery or the like, the inclined surface 11b can reduce the contact load on the anterior capsule Sf when the front supporting portion 11 makes contact with the anterior capsule Sf. Moreover, since the front supporting portion 11 is formed of an elastic material, the front supporting portion 11 is slightly deformed by the force received from the anterior capsule Sf and the contact load between the front supporting portion 11 and the anterior capsule Sf can be reduced further.

Moreover, since a general lens has a diameter of approximately 9 to 10 mm and a thickness of approximately 3.5 to 5.5 mm, the front supporting portion 11 is formed such that an outer circumferential portion has a diameter of 7.0 mm, the opening 11a (an inner circumferential portion 11c) has a diameter of 5.0 mm, and the inclined surface 11b making contact with the anterior capsule Sf has a width of 1.5 mm and a thickness of 0.2 to 0.5 mm.

As illustrated in FIG. 1, the rear supporting portion 12 is a ring-shaped elastic member having an opening 12a at the center and is disposed on the rear side of the front supporting portion 11 in such a manner as to face the front supporting portion 11 in parallel. The rear supporting portion 12 has an inclined surface 12b disposed on the rear surface side so as to be gradually inclined toward the front side as it advances from an inner circumferential portion toward an outer circumferential portion. Due to this, since the rear supporting portion 12 is provided in such a manner as to make contact with the inner surface of the posterior capsule Sb of the lens capsule S of the lens capsule S, the inclined surface 12b can reduce the contact load on the posterior capsule Sb when the rear supporting portion 12 makes contact with the posterior capsule Sb. Moreover, since the rear supporting portion 12 is formed of an elastic material, the rear supporting portion 12 is slightly deformed by the force received from the posterior capsule Sb and the contact load between the rear supporting portion 12 and the posterior capsule Sb can be reduced further. Moreover, the thickness of the rear supporting portion 12 preferably decreases gradually as it advances from the inner circumferential portion toward the outer circumferential portion.

Moreover, the rear supporting portion 12 is formed based on the size of a general lens such that an outer circumferential portion has a diameter of 7.0 mm, an opening 12a (an inner circumferential portion 12c) has a diameter of 5.0 mm, and the inclined surface 12b making contact with the posterior capsule Sb has a width of 1.5 mm and a thickness of 0.6 mm to 0.2 mm as it advances from the inner circumferential portion toward the outer circumferential portion. When the width of the rear supporting portion 12 is set to be larger than the width of the front supporting portion 11 in this manner, since the contact area between the rear supporting portion 12 and the posterior capsule Sb is larger than the contact area between the front supporting portion 11 and the anterior capsule Sf, the rear supporting portion 12 can be arranged stably in the lens capsule S.

As illustrated in FIG. 1, the connecting portion 13 includes a plurality of connecting pieces 131 provided at equal intervals in the circumferential direction of the front supporting portion 11 and the rear supporting portion 12. This connecting piece 131 is a thin plate member formed of an elastic material such as a synthetic resin. One end of the connecting piece 131 is fixed to the rear surface of the front supporting portion 11 in such a manner as to extend in an orthogonal direction or a slightly radially outward direction, and the other end is fixed to the front surface of the rear supporting portion 12 in such a manner as to extend in an orthogonal direction or a slightly radially outward direction.

Moreover, in a natural state in which the connecting piece 131 is not elastically deformed, the connecting portion 13 connects the front supporting portion 11 and the rear supporting portion 12 at a predetermined interval. This predetermined interval is such a length that the connecting piece 131 is slightly bent when this device 1 is arranged in the lens capsule S. Moreover, when the front supporting portion 11 and the rear supporting portion 12 are moved in a direction closer to each other, the connecting portion 13 is bent in such a manner as to expand in a radially outward direction of the front supporting portion 11 and the rear supporting portion 12. Due to this, when the device 10 is arranged in the lens capsule S, a state in which the connecting piece 131 is bent in a radially outward direction is created and elastic force to restore to an original shape is generated. Thus, it is possible to create a state in which the connecting portion 13 applies biasing force in a direction of separating the front supporting portion 11 and the rear supporting portion 12 from each other using the generated elastic force. Moreover, due to the biasing force of the plurality of connecting pieces 131, the connecting portion 13 can extend and expand the anterior capsule Sf and the posterior capsule Sb in the front-back direction efficiently in the entire circumference to open the lens equator Se and applies tension of moderate strength to the Zinn's zonules Z and the lens capsule S.

Moreover, the length and the biasing force of the connecting portion 13 are accommodated so as to have the biasing force corresponding to the tension of the Zinn's zonules Z and the lens capsule S generated during contraction or relaxation of the ciliary muscles Cm of the ciliary bodies C. Due to this, it is possible to continuously apply tension of more moderate strength to the Zinn's zonules Z and the lens capsule S when the device 10 is arranged in the lens capsule S.

Moreover, the connecting portion 13 connects the inner circumferential portion of the front supporting portion 11 and the inner circumferential portion of the rear supporting portion 12. Due to this, since the connecting portion 13 is positioned at the opening edge near the center of the anterior capsule Sf which moves best according to the focus accommodation of the eyes or at the vicinity thereof, it is possible to increase the degree of change in bending of the connecting portion 13 according to the movement of the anterior capsule Sf due to the contraction and relaxation of the ciliary muscles by the focus accommodation. Further, it is possible to effectively change the curvature of the central portion 21 of the optical portion 20 according to the curvature of the connecting portion 13.

[Configuration of Optical Portion]

The optical portion 20 is a flat convex lens formed of an elastic film having a thickness of 5 to 100 µm and a flowable substance is filled therein. The optical portion 20 includes the central portion 21 positioned at the center of the optical portion 20 to refract light and the circumferential portion 22 positioned at the circumference of the optical portion 20.

The optical portion 20 is formed of a material having the same elasticity as the lens of a young person, such as silicon polymer, acrylic polymer, temperature-responsive shape-memory hydrophobic acryl, hydroxyethyl methacrylate, photo-curable resins, or hydrogel. According to this configuration, since the optical portion 20 can be easily elastically deformed when force is applied from the connecting portion 13 to the optical portion 20, it is possible to effectively change the curvature of the optical portion 20.

Moreover, the optical portion 20 has a front ring member 30 provided on a front surface in such a manner of being parallel to the circumferential portion 22 of the optical portion 20 and a rear ring member 31 provided on a rear surface in such a manner of being parallel to the circumferential portion 22 of the optical portion 20.

The front ring member 30 has a plurality of lateral branches 30a provided at equal intervals in the circumferential direction so as to extend obliquely upward from the circumferential portion 22. Each lateral branch 30a is connected to an upper portion 131a of the connecting piece 131. On the other hand, the rear ring member 31 has a plurality of lateral branches 31a provided at equal intervals in the circumferential direction so as to extend obliquely downward from the circumferential portion 22. Each lateral branch 31a is connected to a lower portion 131b of the connecting piece 131.

[Focus Accommodation Function of Accommodating Intraocular Lens]

As illustrated in FIG. 1(a), during distance vision (non-focus accommodation), when the front supporting portion 11 and the rear supporting portion 12 move in the direction closer to each other and the degree of expansion of the connecting portion 13 in the radially outward direction increases, the upper portion 131a and the lower portion 131b of the connecting piece 131 move in the radially outward direction. In this case, the lateral branches 30a and 31a are deformed in such a manner that the attitude thereof changes such that the lateral branch gradually faces in the planar direction from the front-back direction. With such a deformation of the lateral branches 30a and 31a, the front ring member 30 connected to the lateral branch 30a moves in a forward direction, and the downward pressing of the front surface of the circumferential portion 22 decreases gradually and finally disappears substantially. Similarly, the rear ring member 30 connected to the lateral branch 31a moves in a backward direction, and the upward pressing of the rear surface of the circumferential portion 22 of the optical portion 20 decreases and finally disappears substantially.

In this manner, the front ring member 30 rarely presses the front surface of the circumferential portion 22 and the rear ring member 31 rarely presses the rear surface of the circumferential portion 22, whereby force is not applied to the optical portion 20 in the direction of compressing the optical portion 20. Due to this, since the optical portion 20 is elastically deformed by being relaxed up to the original shape, it is possible to decrease the curvature of the central portion 21 of the optical portion 20.

Figure 1B:
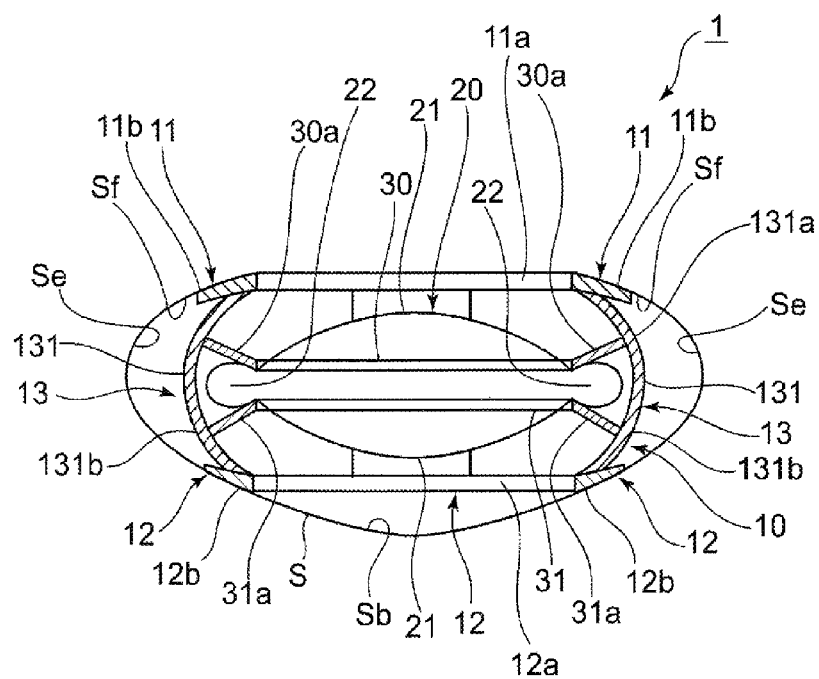
FIG. 1(b) is a longitudinal cross-sectional view illustrating an accommodating intraocular lens according to a first embodiment of the present invention.

On the other hand, as illustrated in FIG. 1(b), during near vision (focus accommodation), when the front supporting portion 11 and the rear supporting portion 12 move in the direction away from each other and the degree of expansion of the connecting portion 13 in the radially outward direction decreases, the upper portion 131a and the lower portion 131b of the connecting piece 131 move in the radially inward direction. In this case, the lateral branches 30a and 31a are deformed in such a manner that the attitude thereof changes such that the lateral branch gradually faces in the front-back direction from the planar direction. With such a deformation of the lateral branches 30a and 31a, the front ring member 30 connected to the lateral branch 30a moves in the backward direction and presses the front surface of the circumferential portion 22 toward the lower side. Similarly, the rear ring member 30 connected to the lateral branch 31a moves in the forward direction and presses the rear surface of the circumferential portion 22 of the optical portion 20 toward the upper side.

In this manner, the front ring member 30 presses the front surface of the circumferential portion 22 toward the lower side and the rear ring member 31 presses the rear surface of the circumferential portion 22 toward the upper side whereby force is applied to the circumferential portion 22 of the optical portion 20 in the direction of compressing the circumferential portion 22. Due to this, since the central portion 21 of the optical portion 20 greatly swells from the front ring member 30 and the rear ring member 31, it is possible to increase the curvature of the central portion 21 of the optical portion 20.

As described above, since force is applied from the connecting portion 13 to the optical portion 20 via the front ring member 30 and the rear ring member 31 in the direction of compressing the optical portion 20 to change the curvature of the optical portion 20, it is possible to exert the focus accommodation power with higher accuracy and sufficiently.

<Second Embodiment>

Next, a second embodiment of the accommodating intraocular lens 1 according to the present invention will be described with reference to FIG. 2.

The optical portion 20 on the front surface is in contact with the inner circumferential portion 11c of the front supporting portion 11 of the lens capsule expanding device 10 whereas the rear ring member 31 on the rear surface is provided in such a manner of being parallel to the circumferential portion 22 of the optical portion 20. The front ring member 30 is not provided unlike the first embodiment.

Figure 2A:
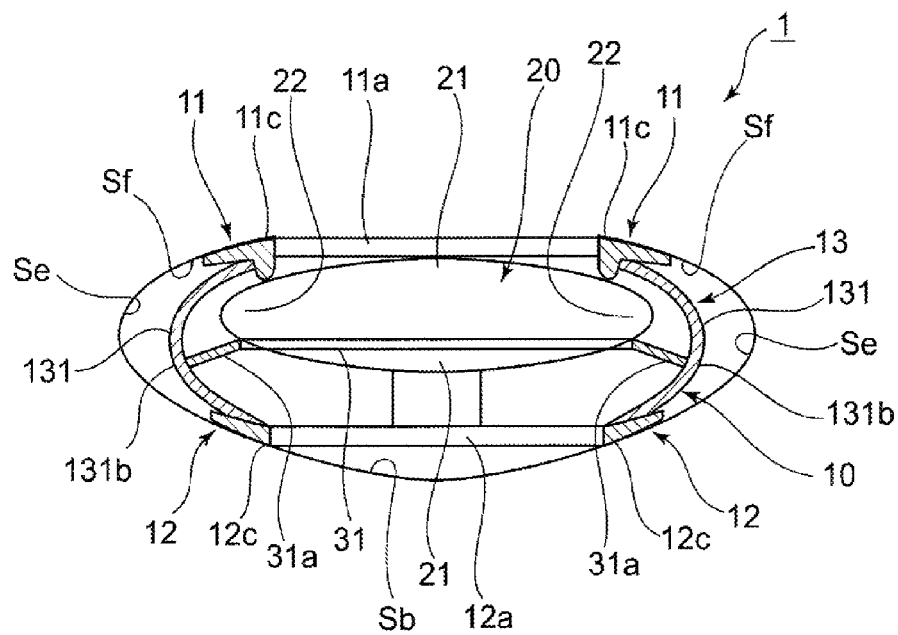
FIG. 2(a) is a longitudinal cross-sectional view illustrating an accommodating intraocular lens according to a second embodiment.

Therefore, as illustrated in FIG. 2(a), during distance vision (non-focus accommodation), when the front supporting portion 11 and the rear supporting portion 12 move in the direction closer to each other and the degree of expansion of the connecting portion 13 in the radially outward direction increases, the lower portion 131b of the connecting piece 131 moves in the radially outward direction. In this case, the lateral branches 31a are deformed in such a manner that the attitude thereof changes such that the lateral branch gradually faces in the planar direction from the front-back direction. With such a deformation of the lateral branches 31a, the rear ring member 31 connected to the lateral branch 31a moves in a backward direction, and the upward pressing of the rear surface of the circumferential portion 22 of the optical portion 2 decreases gradually and finally disappears substantially. As a result, the front supporting portion 11 rarely presses the front surface of the circumferential portion 22 toward the lower side.

In this manner, the front supporting portion 11 rarely presses the front surface of the circumferential portion 22 and the rear ring member 31 rarely presses the rear surface of the circumferential portion 22 whereby force is not applied to the circumferential portion 22 of the optical portion 20 in the direction of compressing the optical portion 20. Due to this, since the optical portion 20 is elastically deformed by being relaxed up to the original shape, it is possible to decrease the curvature of the central portion 21 of the optical portion 20.

Figure 2B:
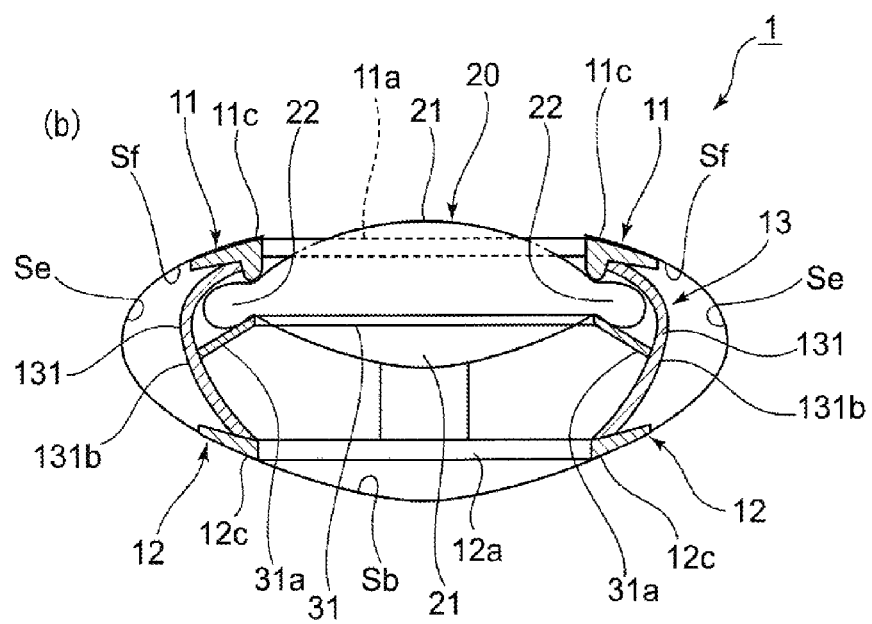
FIG. 2(b) is a longitudinal cross-sectional view illustrating an accommodating intraocular lens according to a second embodiment.

On the other hand, as illustrated in FIG. 2(b), during near vision (focus accommodation), when the front supporting portion 11 and the rear supporting portion 12 move in the direction away from each other and the degree of expansion of the connecting portion 13 in the radially outward direction decreases, the lower portion 131b of the connecting piece 131 moves in the radially inward direction. In this case, the lateral branches 31a are deformed in such a manner that the attitude thereof changes such that the lateral branch gradually faces in the front-back direction from the planar direction. With such a deformation of the lateral branches 31a, the rear ring member 31 connected to the lateral branch 31a moves in the forward direction and presses the rear surface of the circumferential portion 22 of the optical portion 20 toward the upper side.

In this manner, when the optical portion 20 is pressed in the forward direction by the rear ring member 31, the circumferential portion 22 is sandwiched between the rear ring member 31 and the front supporting portion 11, the front surface of the optical portion 20 is pressed downward by the front supporting portion 11, and force is applied to the circumferential portion 22 of the optical portion 20 in the direction of compressing the optical portion 20. Due to this, since the central portion 21 of the optical portion 20 greatly swells from the opening 11a of the front supporting portion 11, it is possible to increase the curvature of the central portion 21 of the optical portion 20.

As described above, since force is applied from the connecting portion 13 to the optical portion 20 via the rear ring member 31 in the direction of compressing the optical portion 20 to change the curvature of the optical portion 20, it is possible to exert the focus accommodation power with higher accuracy and sufficiently.

<Third Embodiment>

Next, a third embodiment of the accommodating intraocular lens 1 according to the present invention will be described with reference to FIG. 3.

Figure 3A:
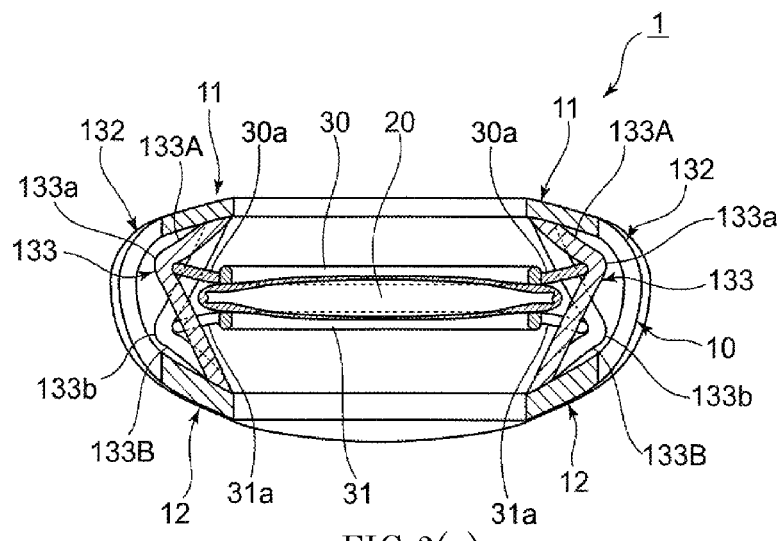
FIG. 3(a) is a longitudinal cross-sectional view illustrating an accommodating intraocular lens according to a third embodiment.
Figure 3B:
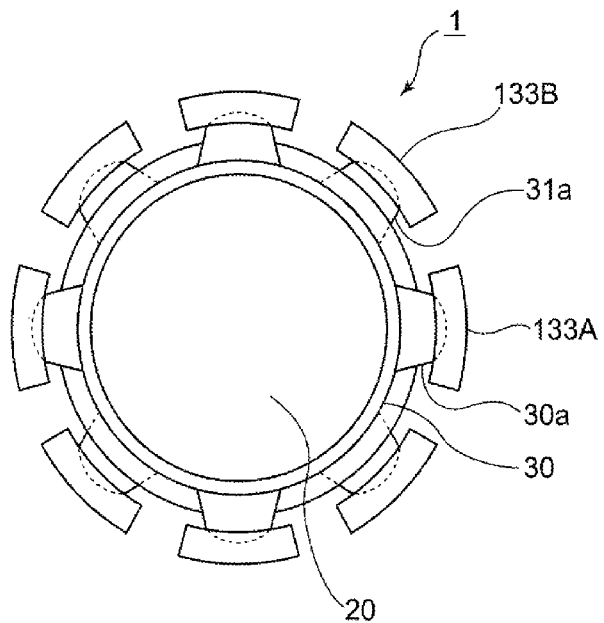
FIG. 3(b) shows a front supporting portion and a rear supporting portion for an accommodating intraocular lens according to a third embodiment.

As illustrated in FIG. 3, the device 10 according to the present embodiment includes a first connecting portion 132 that connects the outer circumferential portions of the front supporting portion 11 and the rear supporting portion 12 and a second connecting portion 133 that connects the inner circumferential portions of the front supporting portion 11 and the rear supporting portion 12. The second connecting portion 133 further includes a front ring connecting portion 133A and a rear ring connecting portion 133B arranged alternately along the circumferential direction.

The front ring connecting portion 133A includes a plurality of connecting pieces provided at equal intervals along the circumferential direction of the front supporting portion 11 and the rear supporting portion 12, a bent portion 133a is formed at a position closer to the front side than the optical portion 10, and the front ring member 30 is connected to the bent portion 133a with the lateral branch 30a interposed.

The rear ring connecting portion 133B includes a plurality of connecting pieces provided at equal intervals along the circumferential direction of the front supporting portion 11 and the rear supporting portion 12, a bent portion 133b is formed at a position closer to the rear side than the optical portion 10, and the rear ring member 31 is connected to the bent portion 133b with the lateral branch 31a interposed.

Therefore, during distance vision (non-focus accommodation), when the front supporting portion 11 and the rear supporting portion 12 move in the direction closer to each other and the degree of expansion of the connecting portion 13 in the radially outward direction increases, the bent portion 133a of the front ring connecting portion 133A and the bent portion 133b of the rear ring connecting portion 133B move in the radially outward direction. In this case, the lateral branches 30a and 31a are deformed in such a manner that the attitude thereof changes such that the lateral branch gradually faces in the planar direction from the front-back direction. With such an attitude deformation of the lateral branches 30a and 31a, the front ring member 30 connected to the lateral branch 30a moves in a forward direction, and the downward pressing of the front surface of the circumferential portion 22 decreases gradually and finally disappears substantially. Similarly, the rear ring member 30 connected to the lateral branch 31a moves in a backward direction, and the upward pressing of the rear surface of the circumferential portion 22 of the optical portion 20 decreases and finally disappears substantially.

In this manner, the front ring member 30 rarely presses the front surface of the circumferential portion 22 and the rear ring member 31 rarely presses the rear surface of the circumferential portion 22, whereby force is not applied to the optical portion 20 in the direction of compressing the optical portion 20. Due to this, since the optical portion 20 is elastically deformed by being relaxed up to the original shape, it is possible to decrease the curvature of the central portion 21 of the optical portion 20.

On the other hand, during near vision (focus accommodation), when the front supporting portion 11 and the rear supporting portion 12 move in the direction away from each other and the degree of expansion of the connecting portion 13 in the radially outward direction decreases, the bent portion 133a of the front ring connecting portion 133A and the bent portion 133b of the rear ring connecting portion 133B move in the radially inward direction. In this case, the lateral branches 30a and 31a are deformed in such a manner that the attitude thereof changes such that the lateral branch gradually faces in the front-back direction from the planar direction. With such an attitude deformation of the lateral branches 30a and 31a, the front ring member 30 connected to the lateral branch 30a moves in the backward direction and presses the front surface of the circumferential portion 22 toward the lower side. Similarly, the rear ring member 30 connected to the lateral branch 31a moves in the forward direction and presses the rear surface of the circumferential portion 22 of the optical portion 20 toward the upper side.

In this manner, the front ring member 30 presses the front surface of the circumferential portion 22 toward the lower side and the rear ring member 31 presses the rear surface of the circumferential portion 22 toward the upper side whereby force is applied to the circumferential portion 22 of the optical portion 20 in the direction of compressing the circumferential portion 22. Due to this, since the central portion 21 of the optical portion 20 greatly swells from the front ring member 30 and the rear ring member 31, it is possible to increase the curvature of the central portion 21 of the optical portion 20.

As described above, since force is applied from the front ring connecting portion 13c and the rear ring connecting portion 13d of the connecting portion 13 to the optical portion 20 via the front ring member 30 and the rear ring member 31 in the direction of compressing the optical portion 20 to change the curvature of the optical portion 20, it is possible to exert the focus accommodation power with higher accuracy and sufficiently.

<Fourth Embodiment>

Next, a fourth embodiment of the accommodating intraocular lens 1 according to the present invention will be described with reference to FIG. 4.

Figure 4:
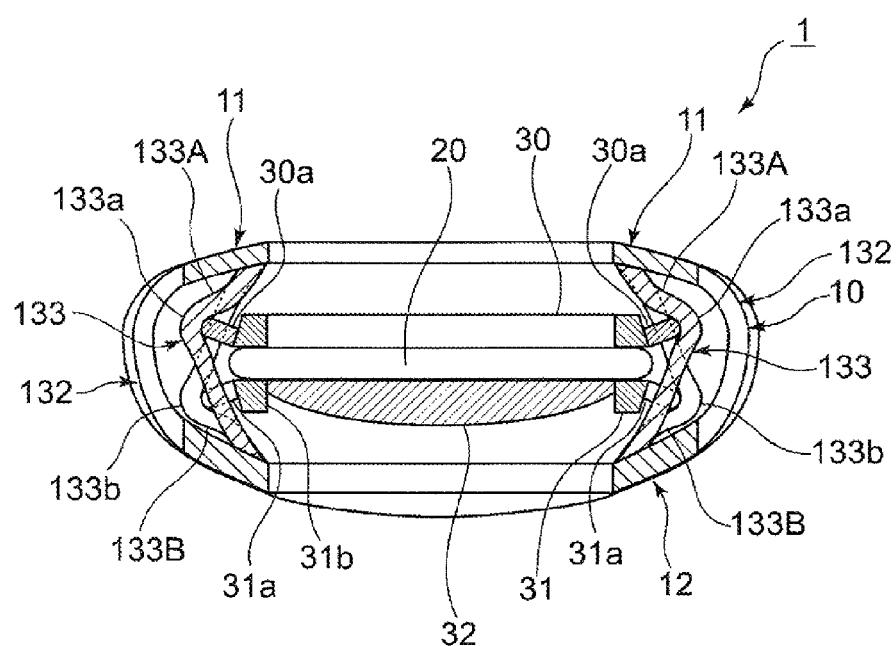
FIG. 4 is a longitudinal cross-sectional view illustrating an accommodating intraocular lens according to a fourth embodiment.
Figure 5A:
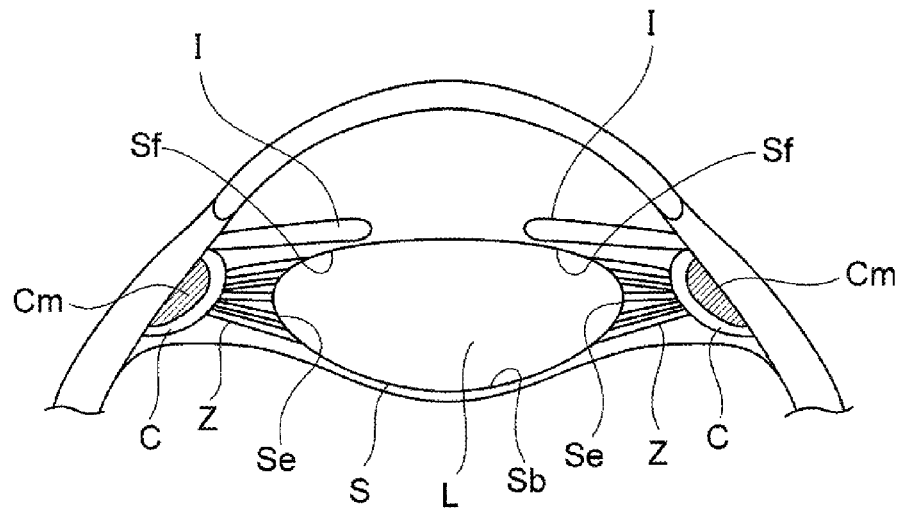
FIG. 5(a) is a side view illustrating the movement of human eyes during focus accommodation.
Figure 5B:
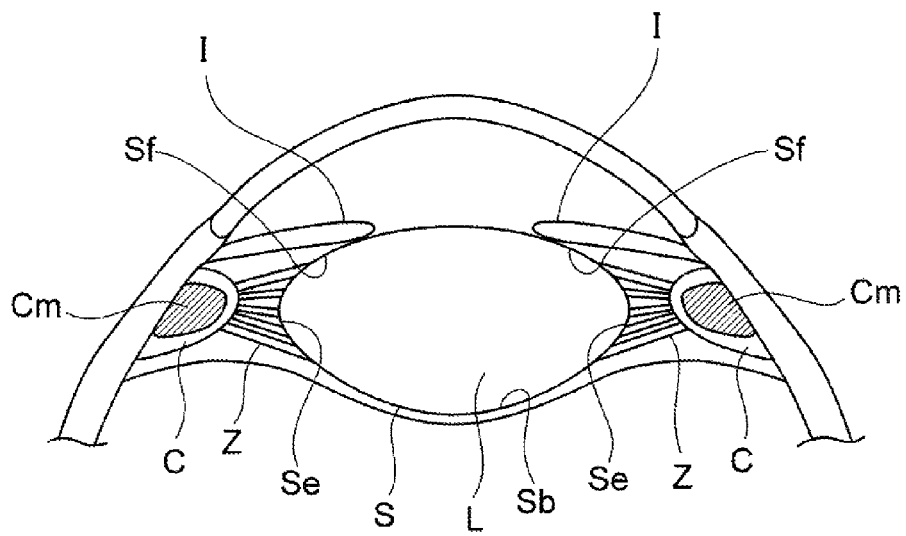
FIG. 5(b) is a side view illustrating the movement of human eyes during focus accommodation.

As illustrated in FIG. 4, in the device 10 according to the present embodiment, a convex lens 32 having a refractive power corresponding to the symptom of a patient is fitted to the opening 31b of the rear ring member 31. According to this configuration, the optical portion which is elastically deformable can be used for the purpose of obtaining the accommodation power mainly and the convex lens 32 provided in the rear ring member 31 can be used for obtaining a refractive power corresponding to the symptom of a patient. Due to this, the optical portion 20 which is elastically deformable is easily folded when it is formed in a flat shape and can be inserted into the eye from a small incised wound of the lens capsule. Moreover, since the convex lens 32 provided in the rear ring member 31 supplements the refractive power after surgery mainly, it is possible to reduce a refraction error (a difference between a target refractive value before surgery and an actual refractive value after surgery) of the refractive power after surgery.

In the respective embodiments described above, the circumferential portion 22 of the optical portion 20 may have a thickness of 20 to 100 μm, the central portion 21 may have a thickness of 5 to 20 μm, and the circumferential portion 22 may be thicker than the central portion 21. Particularly, it is preferable that the optical portion 20 is formed so that the thickness of the elastic film gradually increases as it advances from the circumferential portion 22 toward the central portion 21. According to this configuration, a local deformation of the circumferential portion 22 of the optical portion 20 decreases, and the circumferential portion 22 is likely to be deformed generally uniformly. As a result, the central portion 21 of the optical portion 20 is also likely to be deformed uniformly. Moreover, since the central portion 21 of the optical portion 20 is likely to be deformed due to a small thickness, the curvature of the optical portion 20 can be changed effectively.

Moreover, the optical portion 20 may have a bulging portion formed at a front end and/or a rear end of the thick portion of the elastic film so as to swell toward an inner side.

According to this configuration, when the optical portion 20 is deformed, the circumferential portion 22 of the optical portion 20 is easily constricted near the bulging portion. As a result, since the central portion 21 of the optical portion 20 is likely to swell, the curvature of the optical portion 20 can be changed effectively.

Moreover, the optical portion 20 may be formed so that a refractive index of the flowable substance gradually increases toward the center of the optical portion. For example, the optical portion 20 may be partitioned in the front-back direction and a segment including the center of the optical portion may have a larger refractive index than the refractive indices of the other segments. According to this configuration, since the closer to the center, the larger the refractive index like a human lens, it is possible to create a large change in the refractive index by a small deformation of the optical portion.

Moreover, the optical portion 20 may have a core member formed at the center and having larger rigidity than the flowable substance. According to this configuration, when the optical portion 20 applies force directly or indirectly from the connecting portion, since the flowable substance present around the core substance applies force to the elastic film efficiently, the curvature of the optical portion 20 can be changed efficiently.

Moreover, the core member may be a convex lens having a refractive power corresponding to a symptom of a patient. According to this configuration, the optical portion 20 can be used for the purpose of obtaining the accommodation power mainly, and the convex lens provided in the optical portion 20 can be used for the purpose of obtaining a refractive power corresponding to the symptom of a patient. Moreover, it is possible to reduce a refraction error (a difference between a target refractive value before surgery and an actual refractive value after surgery) of the refractive power after surgery.

Moreover, the optical portion 20 may have an injector for injecting the flowable substance into the optical portion. According to this configuration, after the optical portion 20 is folded and inserted into the lens capsule expanding device in a state in which no or a small amount of the flowable substance is present in the optical portion 20, since the flowable substance can be injected into the optical portion 20 through the injector, it is possible to reduce the size of an incised wound for inserting the accommodating intraocular lens into the lens capsule. Moreover, the refractive power after surgery can be easily adjusted to a target refractive power by injecting or sucking the flowable substance from the injector when a refraction error occurs after surgery.

Moreover, the lens capsule expanding device 10 may have a convex lens or a concave lens provided in the rear supporting portion 12 and having a refractive power corresponding to a symptom of a patient. According to this configuration, the optical portion which is elastically deformable can be used for the purpose of obtaining the accommodation power mainly, and the convex lens or the concave lens provided in the rear supporting portion 12 can be used for the purpose of obtaining a refractive power corresponding to the symptom of a patient. Due to this, the optical portion 20 which is elastically deformable is easily folded when it is formed in a flat shape and can be inserted into the eye from a small incised wound of the lens capsule. Moreover, since the convex lens or the concave lens provided in the rear supporting portion supplements the refractive power after surgery mainly, it is possible to reduce a refraction error (a difference between a target refractive value before surgery and an actual refractive value after surgery) of the refractive power after surgery.

While the embodiments of the present invention have been described with reference to the drawings, the present invention is not limited to the illustrated embodiments. Various changes or modifications can be made to the illustrated embodiments within the same scope as the present invention or its equivalent range.

The invention claimed is:

1. An accommodating intraocular lens (IOL) inserted into a lens capsule from which contents are removed during an ophthalmic surgery, comprising:
   a lens capsule expanding device (10); and
   an optical portion (20) arranged within the lens capsule expanding device, the optical portion comprising an anterior convex surface, a posterior convex surface, a central portion (21), and a circumferential portion (22), the optical portion being elastically deformable, the lens capsule expanding device comprising:
   a front ring-shaped supporting portion (11) comprising an anterior capsular-engaging circumferential surface provided in such a manner as to make contact with an inner surface of an anterior capsule so as to pass light toward a rear side;
   a rear ring-shaped supporting portion (12) comprising a posterior capsular-engaging circumferential surface provided in such a manner as to make contact with an inner surface of a posterior capsule while facing the front supporting portion so as to pass light from a front side toward a rear side; and
   a circumferential connecting portion (13) placed between the front supporting portion and the rear supporting portion, the connecting portion comprising a plurality of connecting pieces (131) provided at equal intervals in the circumferential direction of the front supporting portion and the rear supporting portion and connecting an inner circumferential portion of the front supporting portion and an inner circumferential portion of the rear supporting portion in such a manner as to have biasing force in a direction of separating the front supporting portion and the rear supporting portion from each other, wherein
   due to the biasing force of the connecting portion, the front supporting portion is adapted to press the inner surface of the anterior capsule and the rear supporting portion is adapted to press the inner surface of the posterior capsule,
   the optical portion has a front ring member (30) provided on the anterior convex surface of the optical portion and a rear ring member (31) provided on the posterior convex surface of the optical portion in such a manner of being substantial parallel to the circumferential portion of the optical portion,
   the front ring member is connected to an upper portion (131*a*) of the connecting portion of the lens capsule expanding device via a lateral branch (30*a*) and the rear ring member is connected to a lower portion (131*b*) of the connecting portion of the lens capsule expanding device via a lateral branch (31*a*), and
   force is applied to the optical portion in a backward direction from the connecting portion via the front ring member and force is applied to the optical portion in a forward direction from the connecting portion via the rear ring member according to movement of the connecting portion when the front supporting portion and the rear supporting portion move in a direction away from each other with movement of the lens capsule whereby the optical portion is compressed between the front ring member and the rear ring member and the curvature of the optical portion is changed, wherein the circumferential portion (22) of the optical portion (2) is constricted when the optical portion is compressed between the front ring member and the rear ring member, wherein the optical portion is formed of an elastic film which can be expanded and contracted and has a predetermined thickness, and a flowable optical substance is filled in the elastic film, wherein the elastic film of the circumferential portion (22) of the optical portion is thicker than the elastic film of the central portion (21) of the optical portion, wherein the optical portion is formed so that the thickness of the elastic film gradually increases as it advances from the central portion toward the circumferential portion, wherein the optical portion is formed so that a refractive index of the flowable optical substance gradually increases toward a center of the optical portion.

2. The accommodating intraocular lens according to claim 1, wherein the elastic film of the circumferential portion of the optical portion has a thickness of 20 μm to 100 μm, the elastic film of the central portion of the optical portion has a thickness of 5 μm to 20 μm.

3. The accommodating intraocular lens according to claim 1, wherein the optical portion has an injector for injecting the flowable substance into the optical portion.

* * * * *